United States Patent
Mazzuca

(10) Patent No.: US 10,603,092 B2
(45) Date of Patent: Mar. 31, 2020

(54) STAND-ALONE FUSION IMPLANT SECURED BY IN-LINE FIXATION

(71) Applicant: DEPUY SYNTHES PRODUCTS, INC., Raynham, MA (US)

(72) Inventor: Michael Mazzuca, North Easton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/026,220

(22) Filed: Jul. 3, 2018

(65) Prior Publication Data
US 2018/0317990 A1 Nov. 8, 2018

Related U.S. Application Data

(63) Continuation of application No. 15/402,926, filed on Jan. 10, 2017, now Pat. No. 10,034,699.

(60) Provisional application No. 62/278,590, filed on Jan. 14, 2016.

(51) Int. Cl.
*A61B 17/86* (2006.01)
*A61B 17/70* (2006.01)
*A61B 17/88* (2006.01)

(52) U.S. Cl.
CPC ...... *A61B 17/8625* (2013.01); *A61B 17/7082* (2013.01); *A61B 17/861* (2013.01); *A61B 17/862* (2013.01); *A61B 17/864* (2013.01); *A61B 17/8615* (2013.01); *A61B 17/8685* (2013.01); *A61B 17/8883* (2013.01); *A61B 17/8888* (2013.01); *A61B 17/8605* (2013.01); *A61B 17/8635* (2013.01)

(58) Field of Classification Search
CPC ............ A61B 17/8625; A61B 17/7082; A61B 17/8605; A61B 17/861; A61B 17/8615; A61B 17/862; A61B 17/864; A61B 17/8685; A61B 17/8883; A61B 17/8888; A61B 17/8635
USPC ....... 606/265, 246, 301, 304, 305, 306, 308, 606/309, 316, 318, 323; 623/17.11, 17.16
See application file for complete search history.

(56) References Cited

U.S. PATENT DOCUMENTS

| | | | |
|---|---|---|---|
| 6,010,507 A | 1/2000 | Rudloff | |
| 6,210,442 B1 | 4/2001 | Wing | |
| 6,551,322 B1 | 4/2003 | Lieberman | |
| 7,056,341 B2 | 6/2006 | Crozet | |
| 9,241,806 B2 | 1/2016 | Suh | |
| 2005/0143823 A1 | 6/2005 | Boyd | |
| 2005/0154390 A1* | 7/2005 | Biedermann | A61B 17/7028 128/898 |
| 2006/0129147 A1 | 6/2006 | Biedermann | |
| 2010/0292695 A1* | 11/2010 | May | A61B 17/1642 606/64 |
| 2011/0144703 A1 | 6/2011 | Krause | |

(Continued)

FOREIGN PATENT DOCUMENTS

| | | |
|---|---|---|
| WO | WO 2000016711 | 8/2000 |
| WO | WO 2010028056 | 3/2010 |

*Primary Examiner* — Pedro Philogene
*Assistant Examiner* — David C Comstock

(57) ABSTRACT

Stand alone fusion cage assemblies that can be secured to the adjacent vertebral bodies via an in-line approach that is substantially perpendicular to the anterior wall of the stand alone cage (or substantially parallel to the cage insertion direction).

13 Claims, 16 Drawing Sheets

(56) References Cited

U.S. PATENT DOCUMENTS

| | | | |
|---|---|---|---|
| 2012/0232597 A1* | 9/2012 | Saidha | A61B 17/869 606/305 |
| 2013/0079879 A1* | 3/2013 | Suh | A61B 17/8625 623/17.16 |
| 2013/0190874 A1* | 7/2013 | Glazer | A61F 2/442 623/17.11 |
| 2015/0012048 A1* | 1/2015 | Huebner | A61B 17/864 606/304 |
| 2016/0310190 A1* | 10/2016 | Gonzalez Blohm | A61B 17/70 |
| 2018/0140341 A1* | 5/2018 | Fischer Lokou | A61B 17/7208 |

* cited by examiner

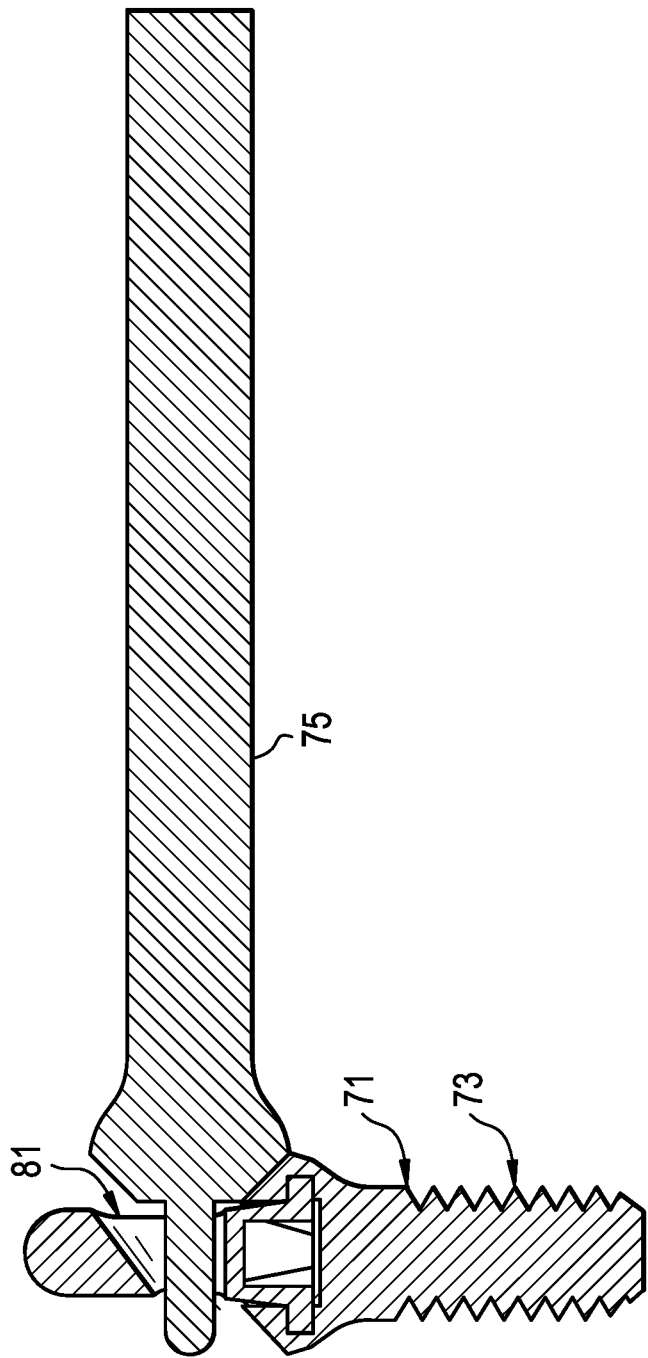

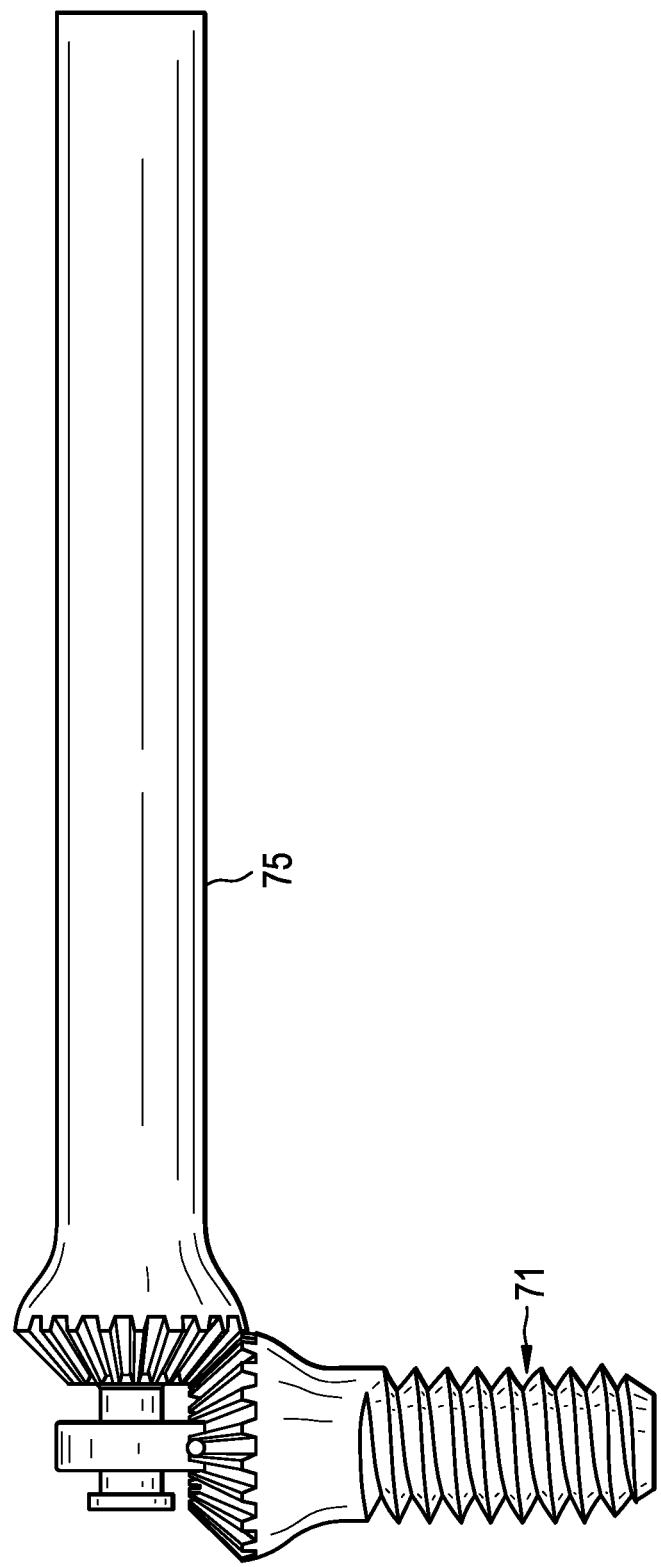

STAND-ALONE FUSION IMPLANT SECURED BY IN-LINE FIXATION

CONTINUING DATA

This patent application is a continuation of and claims priority from co-pending US non provisional application U.S. Ser. No. 15/402,926, filed Jan. 10, 2017, entitled "Stand-Alone Fusion Implant Secured by In-Line Fixation" (Mazzuca et al.), and from US provisional application U.S. Ser. No. 62/278,590, filed Jan. 14, 2016 entitled "Stand-Alone Fusion Implant Secured by In-Line Fixation" (Mazzuca et al.), the specifications of which are incorporated by reference in their entireties.

BACKGROUND OF THE INVENTION

Stand-alone fusion cages have become popular in the field of spinal fusion surgery because they can be used without the need for posterior fixation. In general, at least two fixation devices (such as screws or nails) are passed at an angle through the anterior wall of the stand-alone cage and into the adjacent vertebral bodies, thereby securing the stand-alone cage to the adjacent vertebral bodies.

However, one challenge with these devices is that the need to pass the fixation device at an angle to the cage requires that the inserter also be disposed at an angle, thereby complicating the surgery. In some fusion cases using a stand alone cage, the surgeon must insert the fixation device into the cage at a sharp angle through sometimes challenging approaches. This can be especially difficult for the cervical spine, as the surgeon needs to either deliver the screw down into the inferior vertebral body but may be obstructed by the patient's chin, or deliver the screw up into the superior vertebral body but may be obstructed by the patient's sternum.

Therefore, there is a need to provide a stand alone fusion assembly that can be secured to the adjacent vertebral bodies via an in-line approach that is substantially perpendicular to the anterior wall of the stand alone cage.

U.S. Pat. No. 6,551,322 (Lieberman) discloses using a double helix as a fusion cage.

A number of investigators have attempted to solve the above-stated problem by in-line inserting a helical element into the in-situ cage. See for example, US 2002-0177898 (Crozet) U.S. Pat. Nos. 7,056,341; 6,210,442 (Wing); WO 00/16711 (Meriwether), and WO2010/028056 (Synthes). However, each of these solutions largely involves passing the helical element substantially through the graft-containing region of the cage, thereby reducing the space in the cage available for the critical bone graft.

Although the helix of FIG. 23 of Crozet does not enter the graft space, the height of Crozet's helix (a screw) would need to be only slightly greater than the height of the cage in order to avoid the hitting anterior lips of the adjacent vertebral bodies during insertion. Also, screw backout could be an issue.

Moreover, in each of these prior art solutions, the longitudinal axis of the helix is substantially parallel to the upper and lower surfaces of the cage.

SUMMARY OF THE INVENTION

A number of solutions to the above stated problems have been developed. Stand alone fusion cage assemblies that can be secured to the adjacent vertebral bodies via an in-line approach that is substantially perpendicular to the anterior wall of the stand alone cage (or substantially parallel to the cage insertion direction).

DESCRIPTION OF THE FIGURES

FIGS. 15-16 are perspective and cross-sectional views of a screw-inserter assembly having a projection slidably received in a slot.

FIGS. 17A-B and 18 are side, perspective and cross-sectional views of a screw-inserter assembly having a capped projection slidably received in a slot.

DETAILED DESCRIPTION OF THE INVENTION

For the purposes of the present invention, a "helix" includes structures that have less than a full period of a helix.

Bellows Embodiment

Figure 1A:
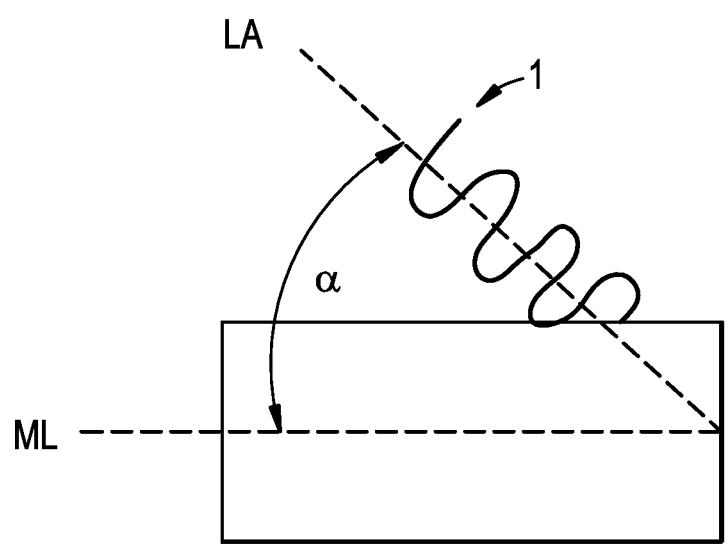
FIG. 1A is a perspective view of a hollow bellows having a helical threadform.

In preferred embodiments, the helix is present in the form of a helical bellows 1, as shown in FIG. 1A.

A traditional metal bellows is a metallic flexible compressible hollow cylindrical structure; the walls are thin and corrugated. The ridges and furrows of the walls facilitate the flexibility of the structure, and as long as the material yield strength is not exceeded the bellow will return to its original form after deformation. Typically the corrugations run parallel to each other and perpendicular to the axis of the cylinder. Metal bellows can be manufactured through forming, welding, or electroforming. Forming bellows involves rolling, deep drawing, or hydroforming. Formed bellows typically have thick walls resulting in reduced flexibility when compared to welded or electroforming. Material choices for formed bellows are restricted to metals with high ductility. Welded bellows are made by edge welding a stack of formed rings. Weld location alternating between the inside and outside edge creates the bellows. Wall thickness is thin and flexibility is high. Electroformed metal bellows are produced by electrodeposition, where a thin layer of metal is electrically deposited on to an aluminum form called a mandrel. The mandrel is precision machined and comprises the geometry of the finished form. Once the desired thickness of material (typically nickel, copper, gold, silver, or a combination of their alloys) is deposited on the mandrel the aluminum is chemically removed leaving behind the finished bellows.

By changing the corrugations from parallel to a helix, a flexible thread form can be produced similar to a metal bellows. The hollow center would allow it to slide over a rod-like structure, and the flexibility would enable it to conform if the rod was curved. A drive feature at one end delivers the means for rotation, and the helical threads provide a method to advance the flexible screw.

Figure 1B:
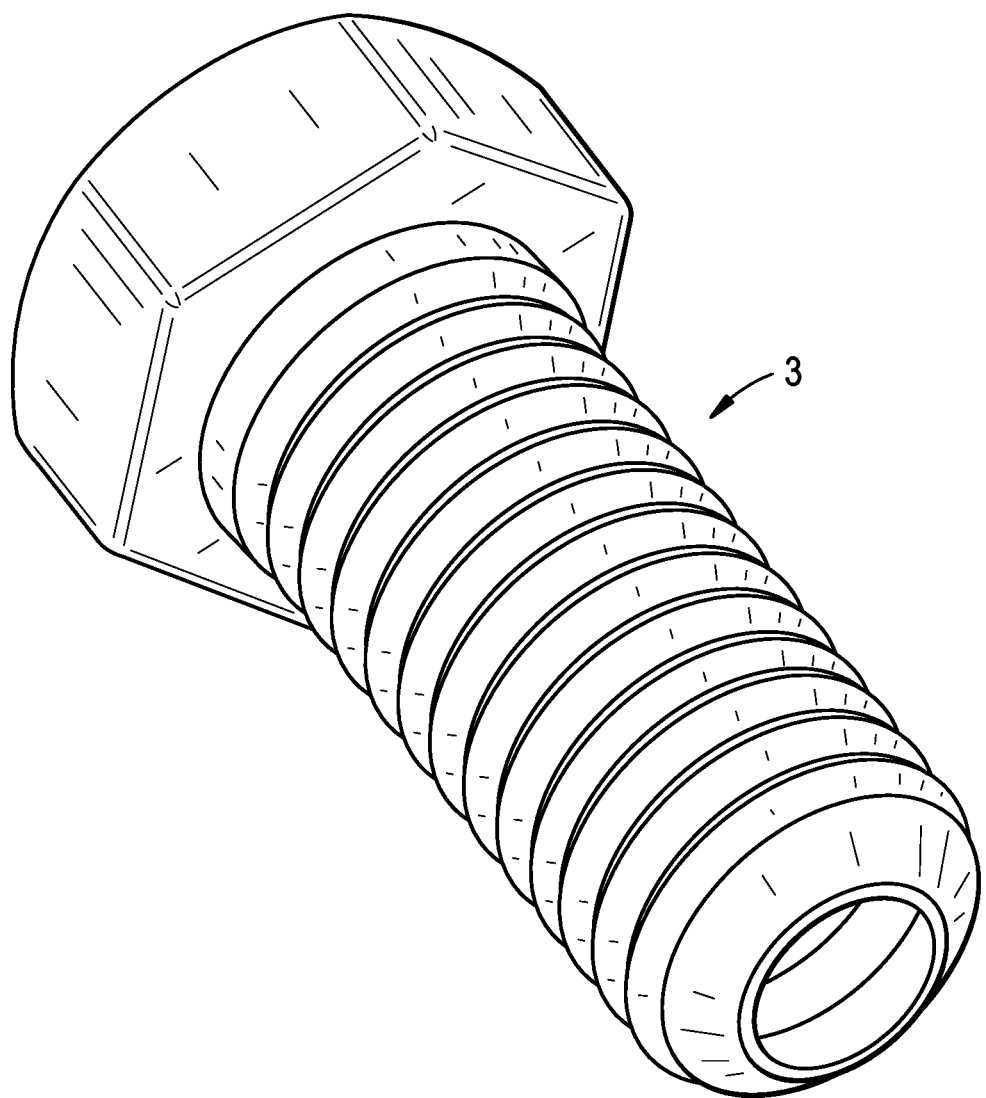
FIG. 1B is an axial cross-sectional view of a hollow bellows having a helical threadform.

FIG. 1B shows a cross section of the helical bellows-type flexible screw 3.

Figure 1C:
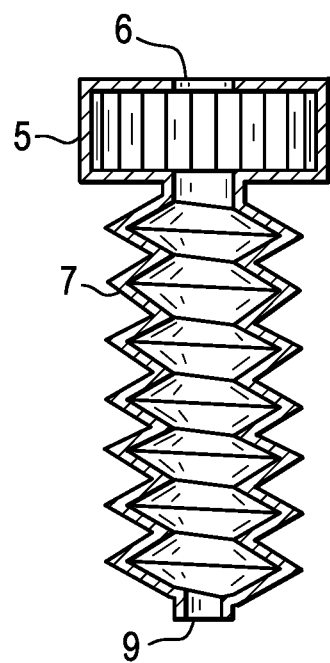
FIG. 1C discloses a bellows screw comprising a proximal head having a hollow center, an intermediate bellows section and a bored distal tip.

FIG. 1C discloses a bellows screw comprising a proximal head 5 having a hollow center 6, an intermediate bellows section 7 and a bored distal tip 9.

The flexible screw could be used to anchor a cage into a vertebral body through a small access site. A traditional straight screw would require a large opening if a high angle screw trajectory was desired. The flexible screw trajectory could be curved, resulting in a much smaller opening for high angle screw placement.

Figure 2A:
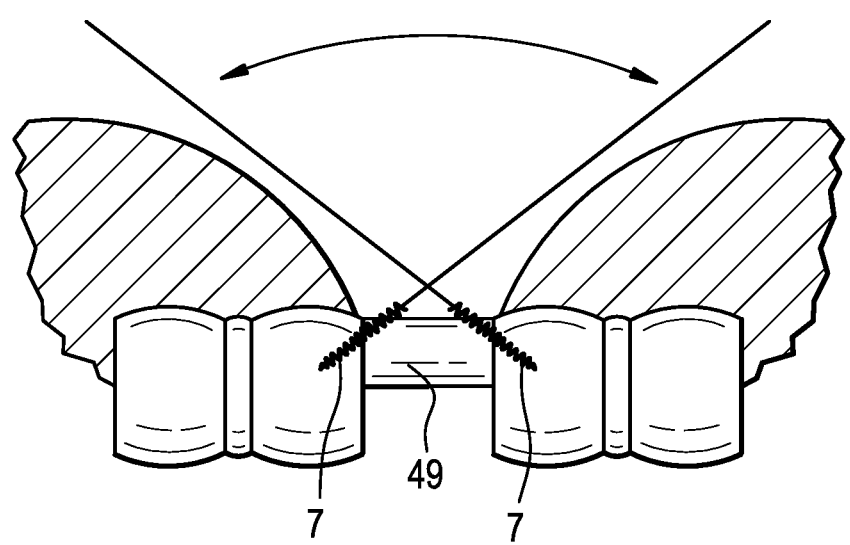
FIG. 2A is a side view of the installation of a conventional stand alone cage.
Figure 2B:
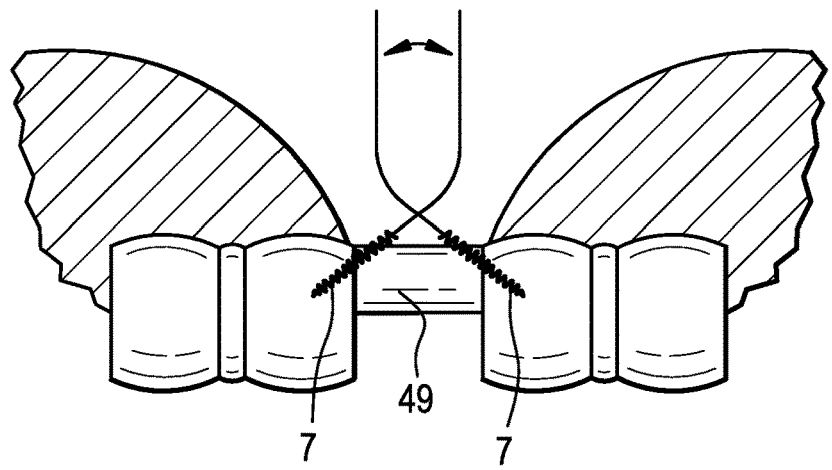
FIGS. 2B and 3 are side views of the installation of a stand alone cage fixed with a hollow bellows screw.

FIGS. 2A and 2B compare the trajectories of the screws 7.

Figure 3:
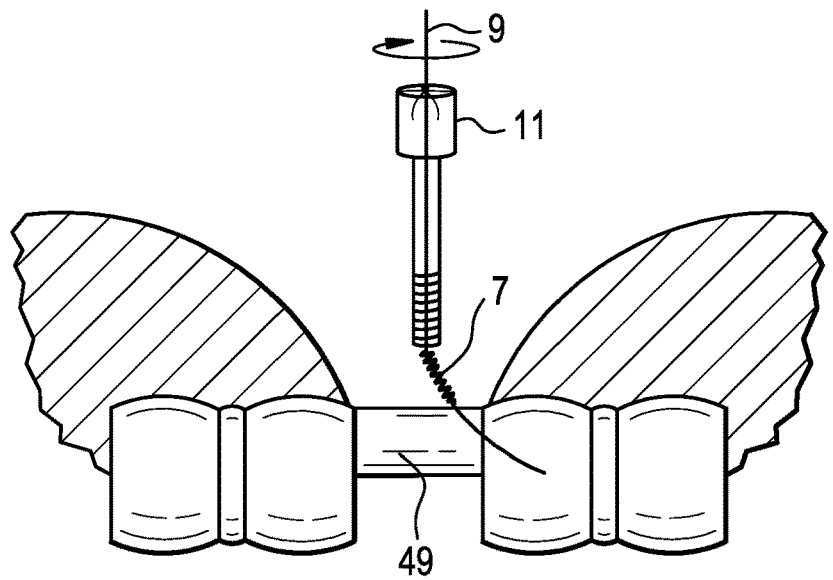
Figure 4:
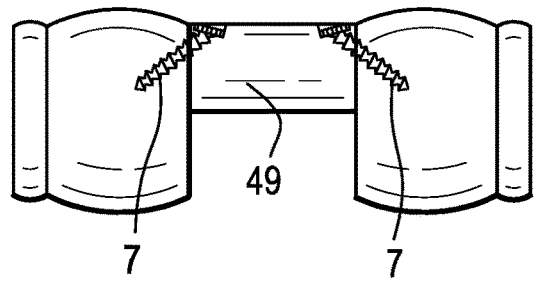
FIG. 4 is a side view of an implanted stand alone cage fixed with a hollow bellows screw.

Now referring to FIG. 3, once the cage is placed between the vertebral bodies a curved stylet 9 is used to create the desired high angle trajectory of the screw. The flexible screw 7 is then placed over the stylet and a cannulated driver 11 engaged with the external drive feature is used to rotate the flexible screw. Once the screw 7 is fully seated the stylet can be removed, see FIG. 4. The head of the screw keeps the cage from dislodging.

Therefore, in accordance with the present invention, there is provided an intervertebral assembly comprising:
a) an intervertebral fusion device having an anterior wall, a posterior wall, and first and second side walls connecting the anterior and posterior walls, an upper bearing surface and a lower bearing surface, the anterior wall having a height and an anterior surface, and a first threaded throughhole extending into the anterior wall from the anterior surface,
b) a fixation device comprising a proximal driving head and a distal flexible bellows having a helical threadform disposed in the first throughhole, wherein the helical threadform threadably mates with the first threaded throughhole.

Preferably, the fixation device bellows has a throughhole extending through the longitudinal axis thereof.

Figure 5:
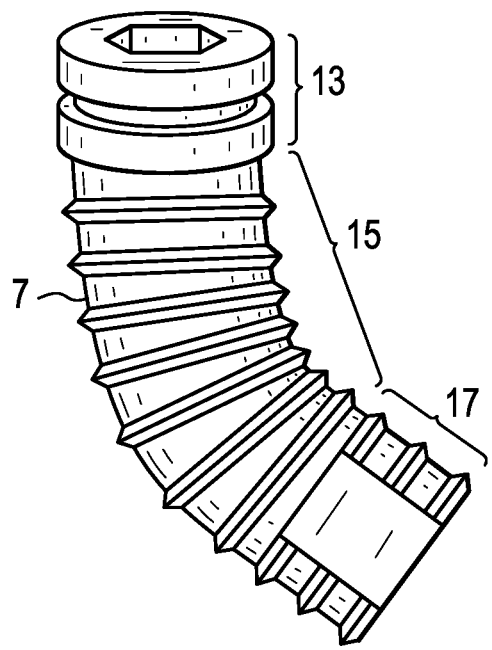
FIG. 5 discloses a preferred screw.

In general, and now referring to FIG. 5, the device is a screw 7 that comprises three sections: a proximal head 13, an intermediate flexible threaded hollow bellows section 15, and a distal tip 17.

Figure 6A:
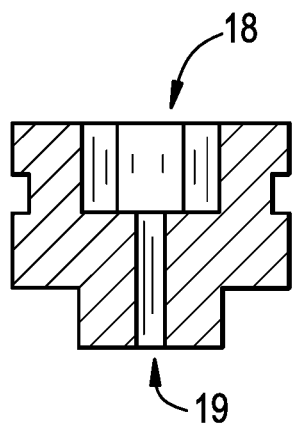
FIGS. 6A-B disclose cross-sectional views of a first set of preferred heads.
Figure 6B:
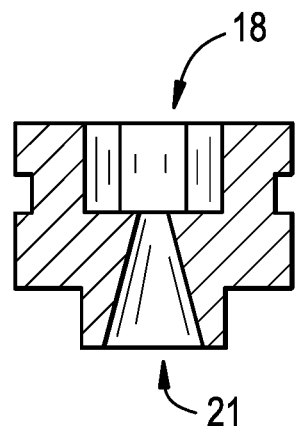

In some embodiments, and now referring to FIGS. 6A-B, the head contains an internal drive feature 18 that mates with an instrument to transfer torque to the screw causing it to advance via the screw threads. The internal drive feature could be a hex, hexlobe, or square. In some embodiments, there is also an axial through-hole in the head to allow the screw to follow a guide wire. The hole could be cylindrical or frustoconical: If the hole is cylindrical 19, its diameter would need to be of sufficient size to allow the screw head to pass over a curved guide wire. If the hole is frustoconical 21, the narrow part of the frustocone would keep the screw head centered but the wide part of the frustocone would allow the head to pass over a curve in the guide wire.

Figure 7A:
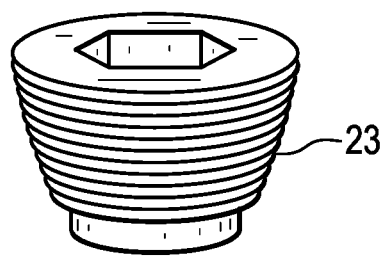
FIGS. 7A-B disclose a second set of preferred heads.
Figure 7B:
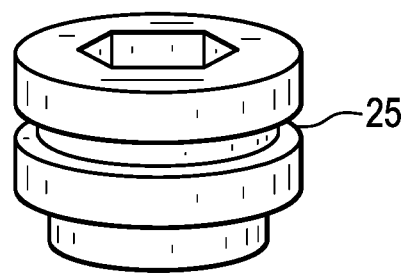

Now referring to FIG. 7A, the screws used to fix the stand-alone fusion cage in place must fasten to the cage to ensure the cage does not migrate and the screws do not back out. One method of securing the screws is to use a tapered threaded head 23. Now referring to FIG. 7B, another embodiment uses a clip that mates with a peripheral groove 25 in the head. Both of these means are established locking mechanisms used in securing the bone screws to plates and/or cages.

Figure 8:
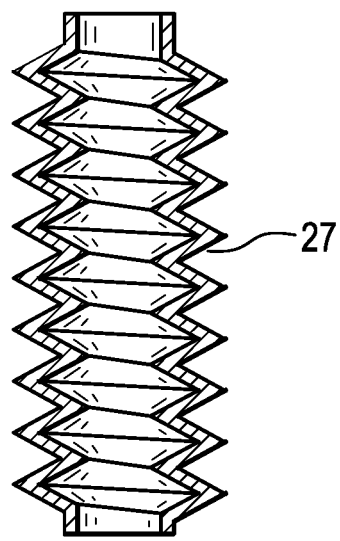
FIG. 8 discloses a preferred bellows.

Now referring to FIG. 8, the bellows section 27 of the screw is flexible and hollow, thereby allowing the screw to slide over and follow the path of a guide wire. Helical threads formed by the bellows enables the screw to axially advance when torque is applied. The outer diameter of the threads should be less than the diameter of the screw head, as this enables the screw threads to pass through the hole in the cage or plate while the screw head cannot.

Figure 9A:
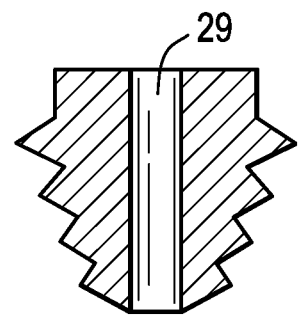
FIGS. 9A-B disclose cross sections of preferred tips.
Figure 9B:
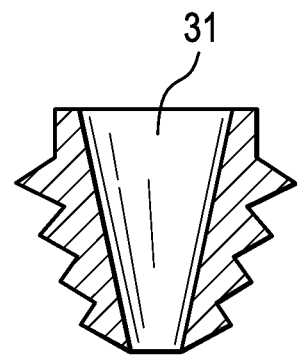

Now referring to FIG. 9A-B, the distal tip of the device is used to guide the screw along the guide wire and incorporates a similar cylindrical 29 or frustoconical 31 axial through-hole as the head. Also preferably incorporated on the tip are tapered threads of the same pitch as the bellows threads. The threads of the tip have an axial cut, thereby creating a flute as a cutting edge.

Figure 10:
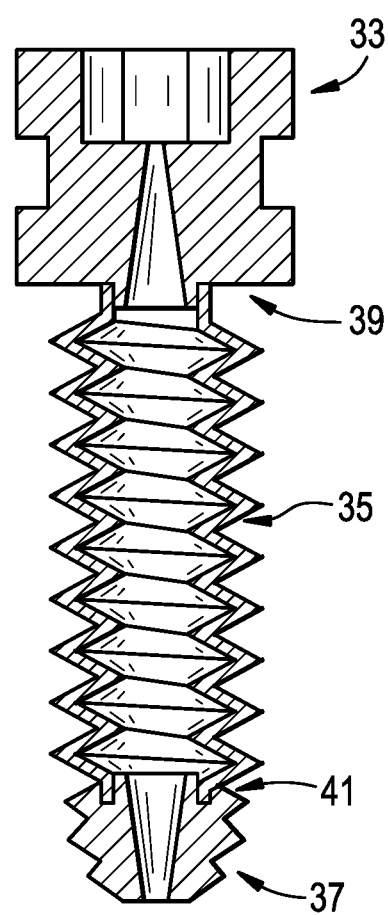
FIG. 10 discloses a preferred embodiment with mechanical joints.

Now referring to FIG. 10, the proximal head 33, intermediate threaded bellows 35, and distal tip 37 can all be made separately and joined together at first 39 and second 41 joints to create the screw. Methods of joining could include welding, brazing, gluing, or mechanical swaging.

The curved guide wire should be of a material that is stiff and strong enough to maintain its curve while being inserted through the cage or plate and into the vertebral body. Pre-curved wires would be preferred to ensure the screw can flex appropriately to conform to the guide wire.

Figure 11A:
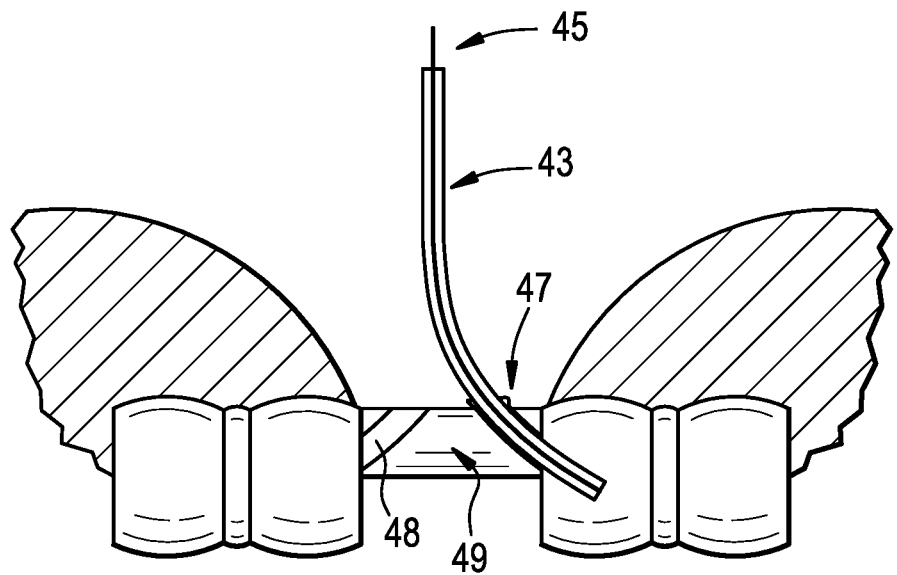
FIGS. 11A-B disclose a preferred method of inserting the screw.
Figure 11B:
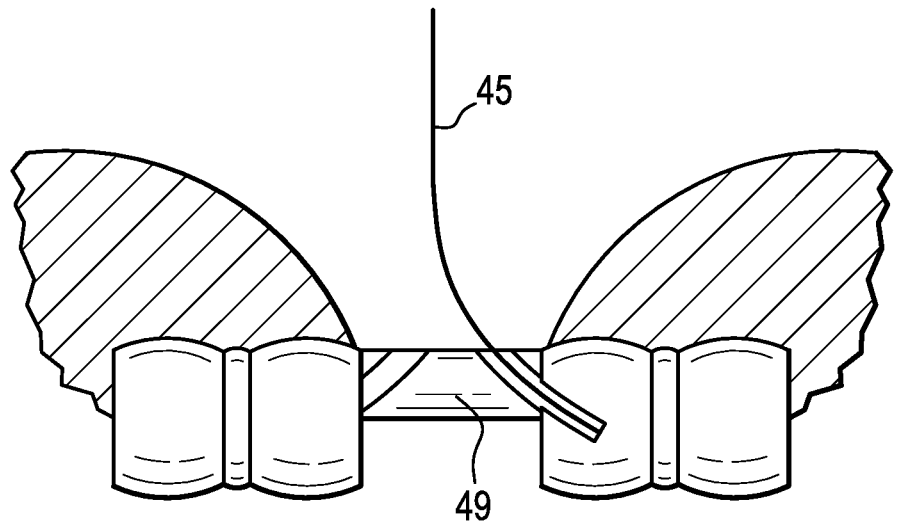

Now referring to FIGS. 11A-B, a sleeve 43 can be used over the guide wire 45 to create a slightly larger path in the vertebral body. Once the sleeve is removed from the guide wire, the extra space left by the sleeve will assist with screw insertion.

A centering guide 47 can be inserted into a hole 48 in a plate or cage 49 to ensure the guide wire is located centrally in the screw.

Spherical Hex Embodiment

Figure 12:
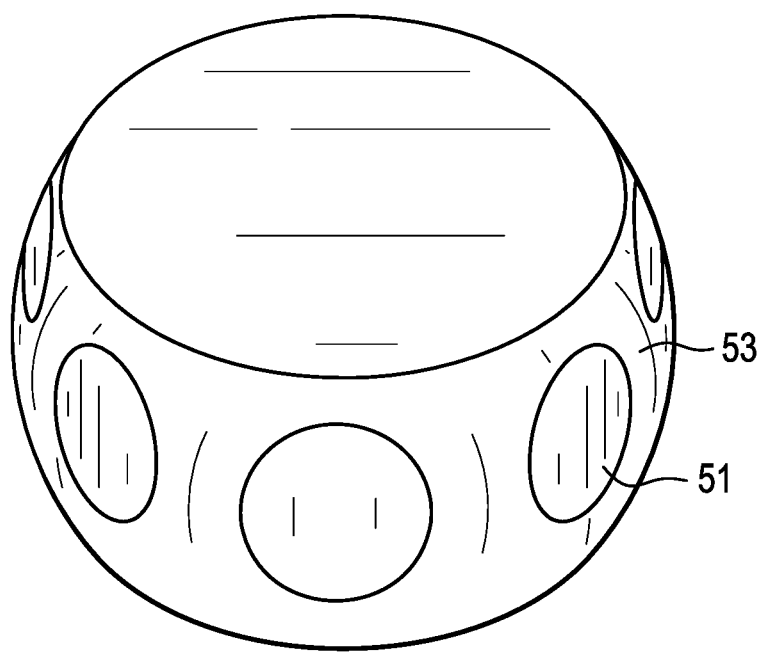
FIG. 12 is a perspective view of a conventional spherical hex.
Figure 13:
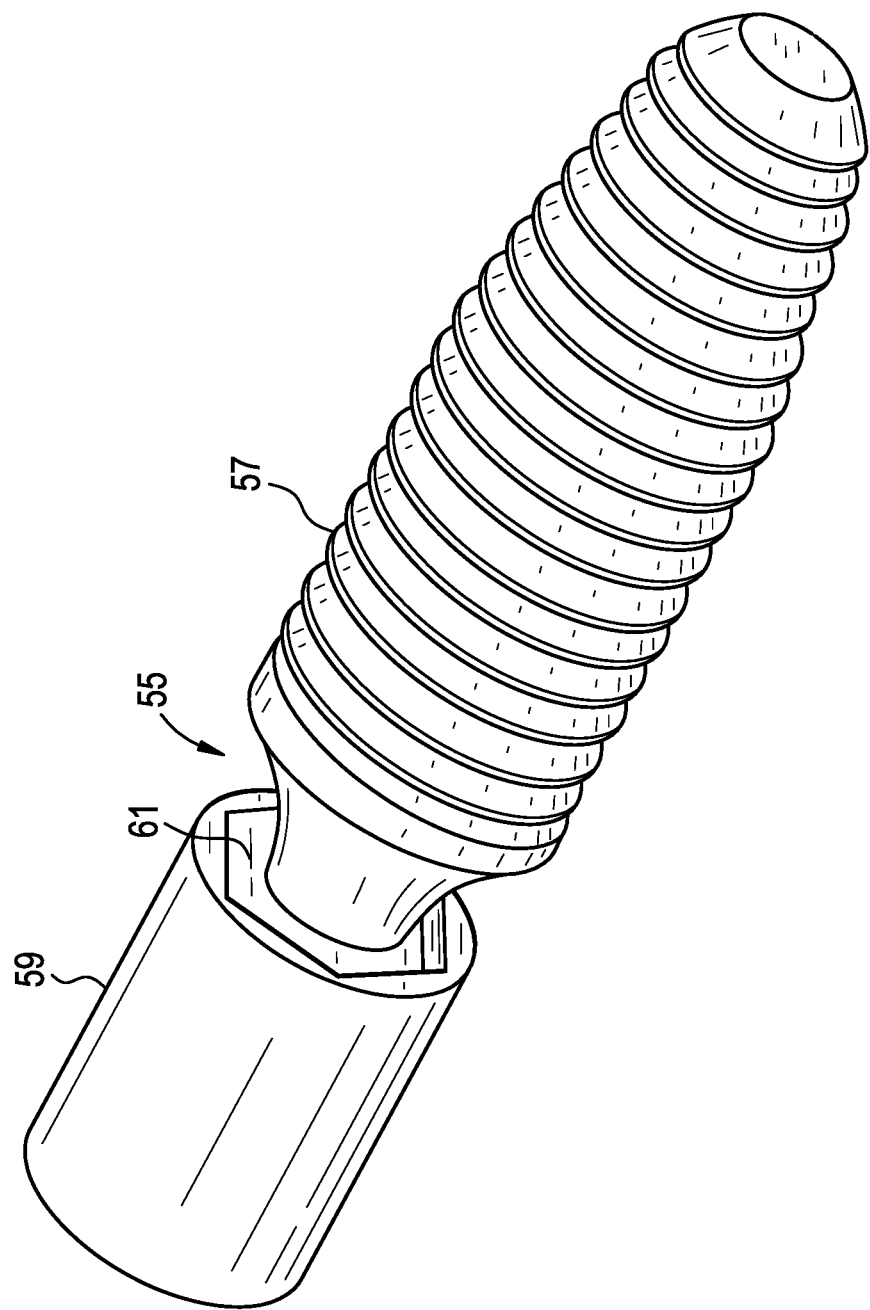
FIGS. 13-14 are perspective and cross-sectional views of a screw-inserter assembly having a spherical hex joint.
Figure 14:
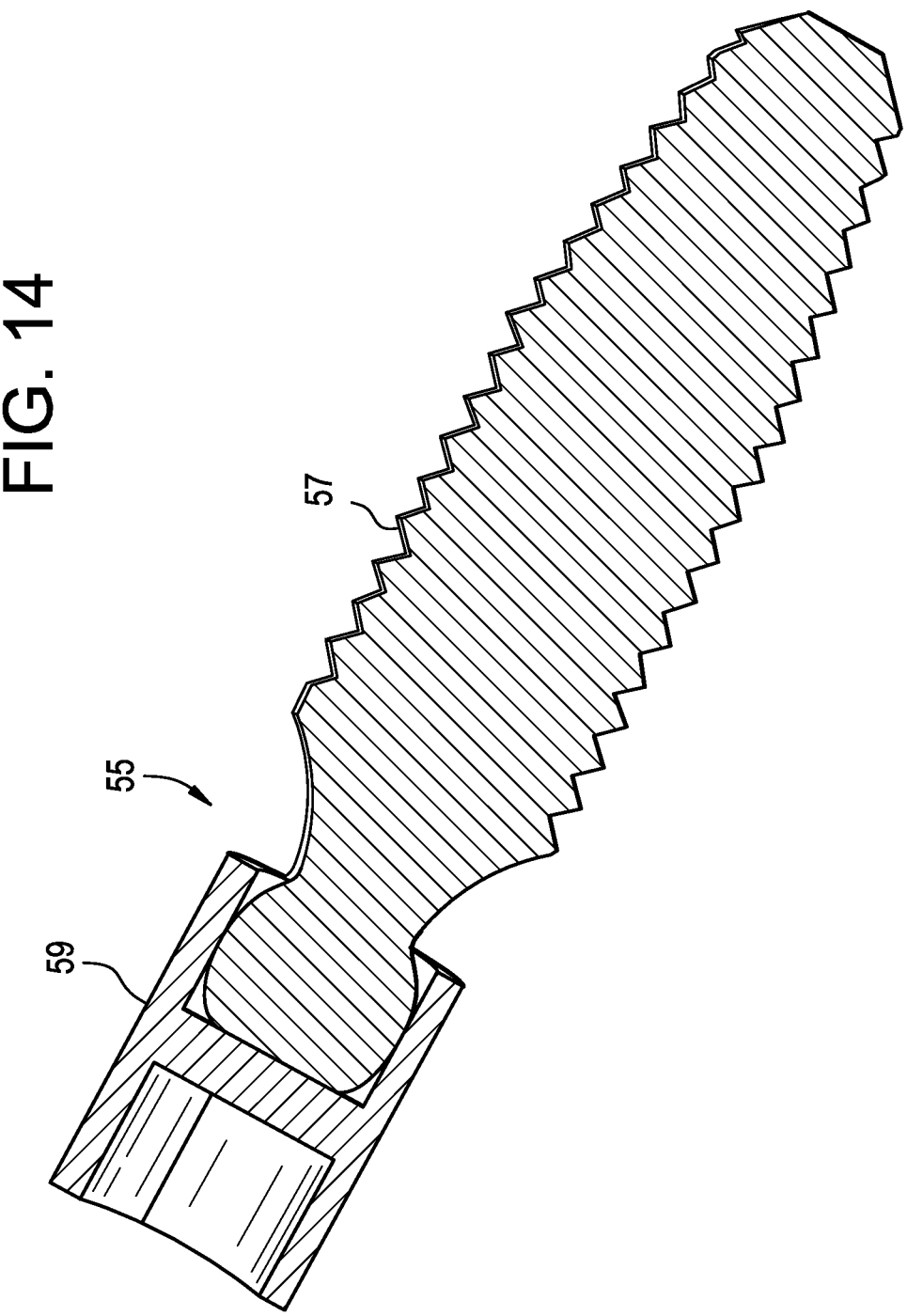
Figure 15:
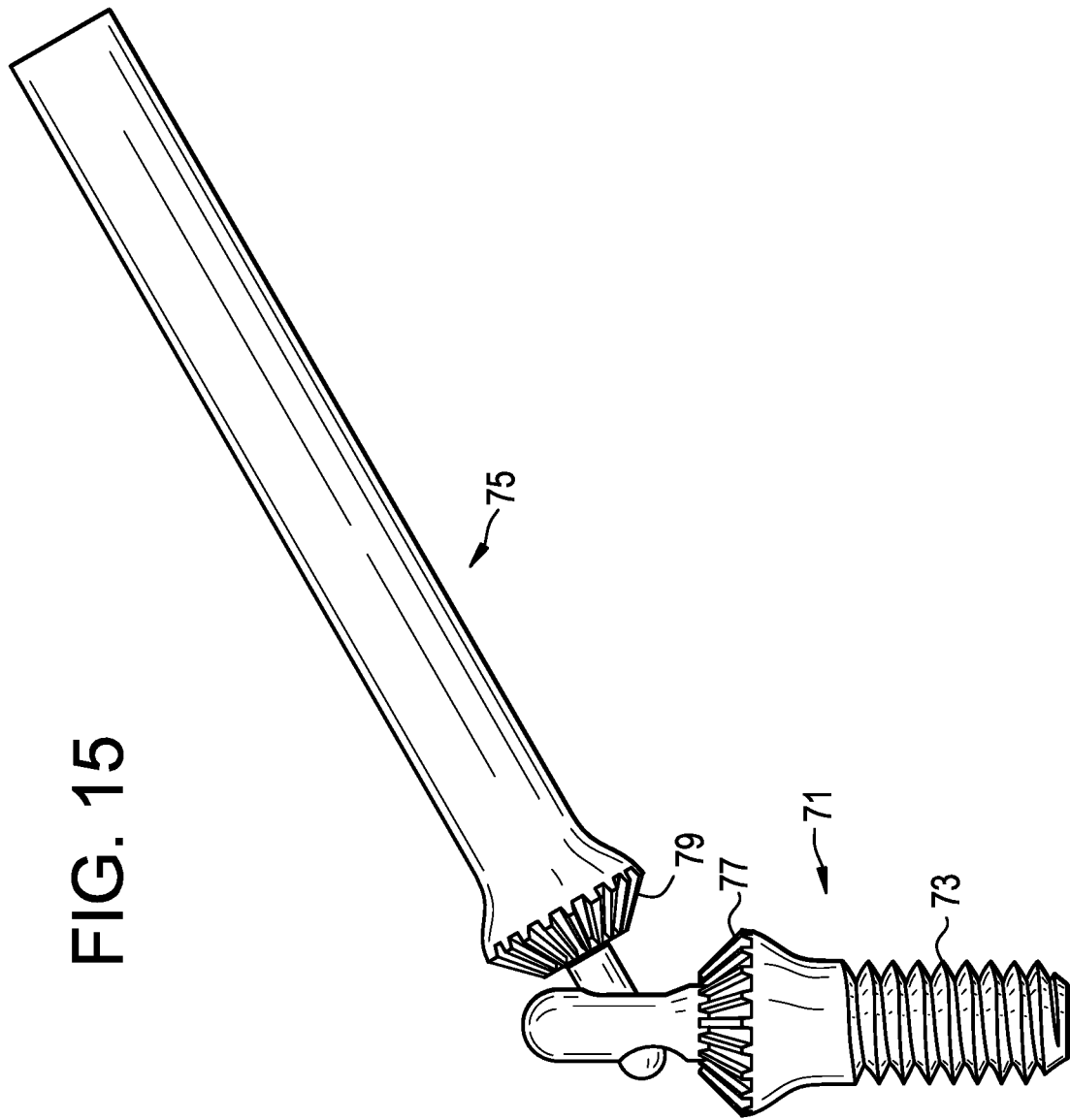
Figure 17B:
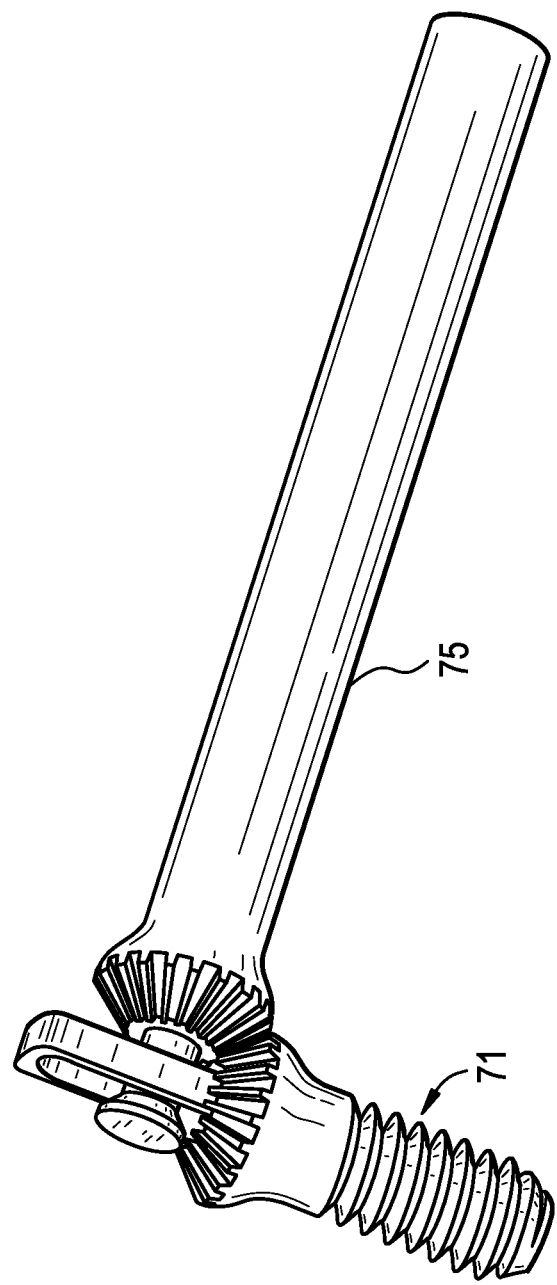
Figure 18:
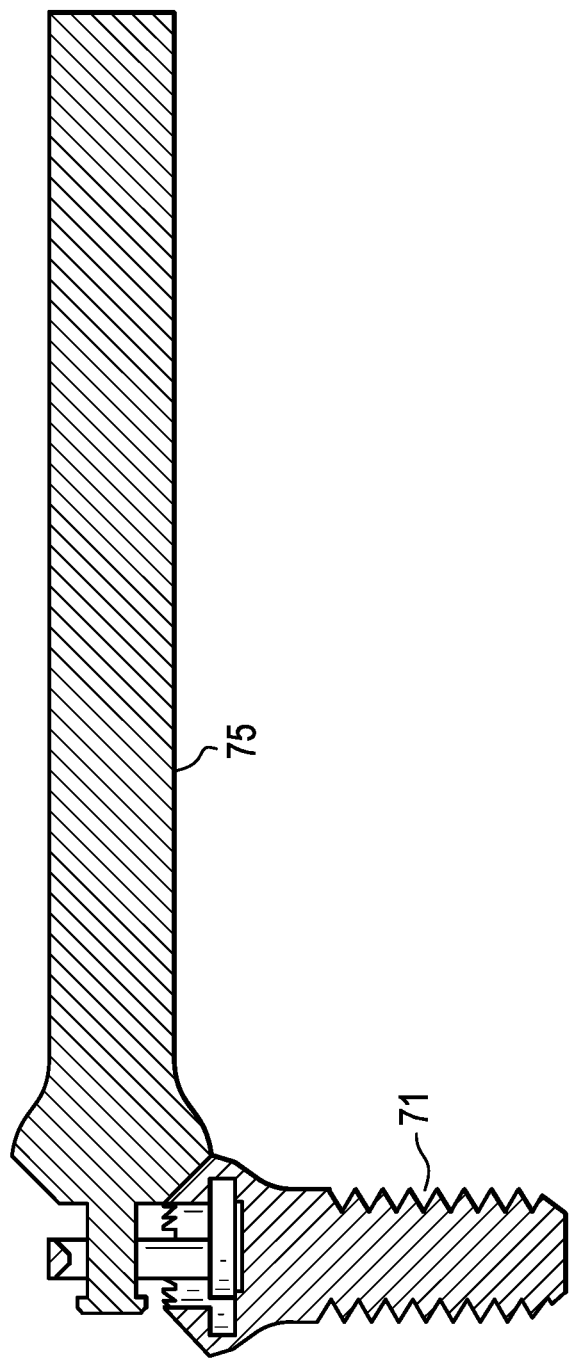

In another embodiment, and now referring to FIGS. 12-14, there is provided an inserter-device assembly wherein the driver head of the fixation device incorporates a spherical hex. For the purposes of the present invention, a "spherical hex" shape is a spherical surface having six equally-spaced flats 51 around a perimeter of the spherical surface 53. When a traditional ball and socket joint is modified so that the spherical hex replaces the ball and a hexagonal socket replaces the spherical socket, the resultant design allows the transmission of torque between the two components. The proximal end of the threaded "screw" component can be either a male (head) or female (socket) end. A spring/ball plunger or other means can be used to apply friction to the spherical hex head to keep the two components rigidly engaged. Once assembled, the mouth of the hex socket is deformed to close around the base of the spherical hex head to ensure the two components do not disassemble. The size and shape of the geometry of the neck at the base of the spherical hex head helps determine how much angulation is allowed. Although a hex has been described, any cross section (square, pentagon, octagon, etc.) with flats to engage a corresponding socket which allows the transmission of torque is envisioned.

Therefore, in accordance with the present invention, there is provided an intervertebral assembly comprising:
 a) an intervertebral fusion device having an anterior wall, a posterior wall, and first and second side walls connecting the anterior and posterior walls, an upper bearing surface and a lower bearing surface, the anterior wall having a height and an anterior surface, and a first threaded throughhole extending into the anterior wall from the anterior surface,
 b) a fixation device comprising a proximal driving head and a distal shaft having a threadform disposed in the first throughhole, wherein the threadform threadably mates with the first threaded throughhole, and
 c) an inserter having a distal endportion that mates with the driving head,
wherein the distal endportion of the inserter and the driving head form a joint 55 comprising i) a head element 57 comprising a spherical surface having a plurality of flats spaced equidistantly along a perimeter of the spherical surface, and ii) a socket element 59 comprising a mating surface mating with the plurality of flats 61.

Preferably, the distal endportion of the inserter and the driving head form a spherical hex joint.

Also in accordance with the present invention, there is provided an intervertebral assembly comprising:
 a) an intervertebral fusion device having an anterior wall, a posterior wall, and first and second side walls connecting the anterior and posterior walls, an upper bearing surface and a lower bearing surface, the anterior wall having a height and an anterior surface, and a first threaded throughhole extending into the anterior wall from the anterior surface,
 b) a fixation device comprising a driving head and a distal shaft having a longitudinal axis and a threadform disposed in the first throughhole, wherein the driving head comprises a spherical surface having a plurality of flats spaced equidistantly along a perimeter of the spherical surface, wherein the perimeter is substantially perpendicular to the longitudinal axis of the shaft, and
wherein the threadform threadably mates with the first threaded throughhole.

In another embodiment, a cable is attached between the distal screw end and a proximal socket. The ends of the cable can be welded in place to rigidly attach the socket to the screw. The cable provides flexibility yet allows the transmission of torque between the socket and screw.

Slidable Gear Joint Embodiment

In another embodiment, and now referring to FIGS. 15-18, there is i) a bone anchor 71 (or screw) having a shaft defining a first longitudinal axis and helical threads 73 extending from the shaft, and ii) a driver 75 also having a second longitudinal axis, wherein the proximal endportion of the bone anchor slidingly interfaces with the distal endportion of the driver in a manner whereby the longitudinal axis of the driver and the longitudinal axis of the screw are not necessarily collinear or parallel, but rather form an oblique angle. The distal endportion of the driver and the proximal endportion of the bone anchor each contains a mating gear element 77, 79 so that rotation of the driver resulting in driving the screw through the transmission of torque through the gear. The driver and screw being positioned at an oblique angle allows the driving to proceed without the requirement of in-line force transmission. In some embodiments, the torque is transmitted by a beveled gear mechanism having teeth on the screw and teeth on the drive. Rotation of the driver about its longitudinal axis will cause rotation of the screw about its longitudinal axis.

The mechanism for keeping the driver and screw engaged (while the driver drives the screw) could take any of several forms. The proximal endportion of the Screw can have a rotatable post which extends proximally from the screw head along the screw axis, wherein the post is retained by and rotatable along with the body of the screw. The post preferably also has a transverse opening 81 (such as a slot or a hole) to accept a distal portion of the driver tip.

Therefore, in accordance with the present invention, there is provided an intervertebral assembly comprising:
 a) an intervertebral fusion device having an anterior wall, a posterior wall, and first and second side walls connecting the anterior and posterior walls, an upper bearing surface and a lower bearing surface, the anterior wall having a height and an anterior surface, and a first threaded throughhole extending into the anterior wall from the anterior surface,
 b) a fixation device comprising i) an elongate proximal projection defining a longitudinal axis and having a throughhole extending transversely therethrough, ii) an intermediate driving head having a first geared surface facing proximally, and iii) a distal shaft having a threadform disposed in the first throughhole, wherein the threadform threadably mates with the first threaded throughhole, and
 c) an inserter having i) an elongate distal endportion, ii) a proximal endportion having a handle, and iii) an intermediate portion therebetween having a second geared surface that mates with the first geared surface of the proximal driving head,
wherein the elongate distal endportion of the inserter is slidably received in the throughhole of the proximal projection of the fixation device.

Preferably, the proximal projection of the fixation device is detachable.

In a first preferred embodiment, the throughhole of the proximal projection of the fixation device defines:
 a) a proximal inner surface disposed at an angle to the longitudinal axis of the elongate proximal projection, wherein the angle us between about 30 and 60 degrees, and
 b) a distal inner surface disposed substantially perpendicularly to the longitudinal axis of the elongate proximal projection, In a second preferred embodiment the elongate distal endportion of the inserter has a distal head thereon.

I claim:

1. A method of treating a spine, comprising the steps of:
 i) inserting into a disc space an intervertebral fusion device having an anterior wall, a posterior wall, and first and second side walls connecting the anterior and posterior walls, an upper bearing surface and a lower bearing surface, the anterior wall having a height and an anterior surface, and a first threaded throughhole extending into the anterior wall from the anterior surface,
 ii) disposing into the first threaded throughhole a fixation device comprising a proximal head and an intermediate flexible bellows having a corrugated wall comprising a helical threadform,
wherein the helical threadform threadably mates with the first threaded throughhole.

2. The method of claim 1 wherein the proximal head of the device comprises an internal drive feature.

3. The method of claim 1 wherein the proximal head of the device comprises an axial through hole.

4. The method of claim 3 wherein the axial through hole is cylindrical.

5. The method of claim 3 wherein the axial through hole is frustoconical.

6. The method of claim 1 wherein the proximal head of the device is tapered and threaded.

7. The method of claim 1 wherein the proximal head of the device has a peripheral groove.

8. The method of claim 1 further comprising c) a guidewire extending through the fixation device.

9. The method of claim 8 further comprising d) a sleeve, wherein the guide wire extends through the sleeve.

10. The method of claim 9 further comprising e) a centering guide disposed in a hole in the intervertebral fusion device, wherein the sleeve extends through the centering guide.

11. The method of claim 1 wherein the device further comprises a distal tip.

12. The method of claim 11 wherein the distal tip has a tapered thread.

13. The method of claim 11 wherein the head, bellow and tip are independent elements joined by first and second joints.

* * * * *